US00PP35814P2

(12) United States Plant Patent
Kolster et al.

(10) Patent No.: US PP35,814 P2
(45) Date of Patent: May 21, 2024

(54) ***HYDRANGEA* PLANT NAMED 'HOKOMAPFLOY'**

(50) Latin Name: *Hydrangea macrophylla*
Varietal Denomination: Hokomapfloy

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: KOLSTER HOLDING BV, Boskoop (NL), part interest; HORTEVE BREEDING BV, Aalsmeer (NL), part interest ( * ) Notice: Subject to any disclaimer, the term of this patent is extended or adjusted under 35 U.S.C. 154(b) by 0 days.

(21) Appl. No.: 18/226,592

(22) Filed: Jul. 26, 2023

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J Aguirre

(57) ABSTRACT

A new cultivar of *Hydrangea macrophylla* plant named 'Hokomapfloy' that is characterized by its compact, densely branched and rounded plant habit, its clear pink inflorescences that as also perform well under bluing conditions, its mophead inflorescences with a hard (sturdy) texture, its suitability as a potted plant and for cut flowers, and its unique cup-shaped sterile flowers.

2 Drawing Sheets

Botanical classification: *Hydrangea macrophylla.*
Varietal denomination: 'Hokomapfloy'.

BACKGROUND OF THE INVENTION

The present invention relates to a new and distinct cultivar of *Hydrangea macrophylla* and will be referred to hereafter by its cultivar name, 'Hokomapfloy'. 'Hokomapfloy' represents a new bigleaf *Hydrangea*, a perennial shrub grown for use in the landscape, as a potted plant, and as a cut flower.

'Hokomapfloy' derived from an ongoing controlled breeding program directed by the Inventors. The goal of the breeding program included developing a new cultivar of *Hydrangea* with hard (sturdy) textured flowers and suitability as a potted plant and as a cut flower.

'Hokomapfloy' arose from a controlled cross made by the Inventors in Boskoop, The Netherlands in May of 2006 between unnamed and unpatented proprietary plants in the Inventor's breeding program, reference no. 03-058-01 as the female parent and reference no. 03-056-01 as the male parent. The new cultivar was selected as a single unique plant in May of 2008 from the resulting seedling from the above cross.

Asexual propagation of the new cultivar was first accomplished by stem cuttings under the direction of the Inventors in July of 2008 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomapfloy' as a unique cultivar of *Hydrangea macrophylla.*

1. 'Hokomapfloy' exhibits a compact, densely branched and rounded plant habit.
2. 'Hokomapfloy' exhibits clear pink inflorescences that as also perform well under bluing conditions.
3. 'Hokomapfloy' exhibits mophead inflorescences with a hard (sturdy) texture.
4. 'Hokomapfloy' exhibits suitability as a potted plant and for cut flowers.
5. 'Hokomapfloy' exhibits unique cup-shaped sterile flowers.

Both the female and male parent of 'Hokomapfloy' differ from 'Hokomapfloy' in having inflorescences that are red in color and sterile flowers that are less cup-shaped. 'Hokomapfloy' can be most closely compared to the *Hydrangea macrophylla* cultivars 'Verena' (not patented) and 'Magical Opal' (U.S. Plant Pat. No. 20,483). Both 'Verena' and 'Magical Opal' are similar to 'Hokomapfloy' in having pink inflorescences that perform well under bluing conditions and suitability for growing as a cut flower. Both 'Verena' and 'Magical Opal' differ from 'Hokomapfloy' in having less sterile flowers per inflorescence, sterile flowers that are less cup-shaped, and inflorescences that are softer in texture.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include a website listing by Monrovia.

BRIEF DESCRIPTION OF THE DRAWINGS

The accompanying color photographs illustrate the overall appearance and distinct characteristics of the new *Hydrangea*. The photographs were taken of plants 3 years in age as grown outdoors in 5-liter containers in Boskoop, The Netherlands.

The photograph in FIG. 1 provides a side view of the inflorescences 'Hokomapfloy' in bloom when grown under bluing conditions.

Figure 1:
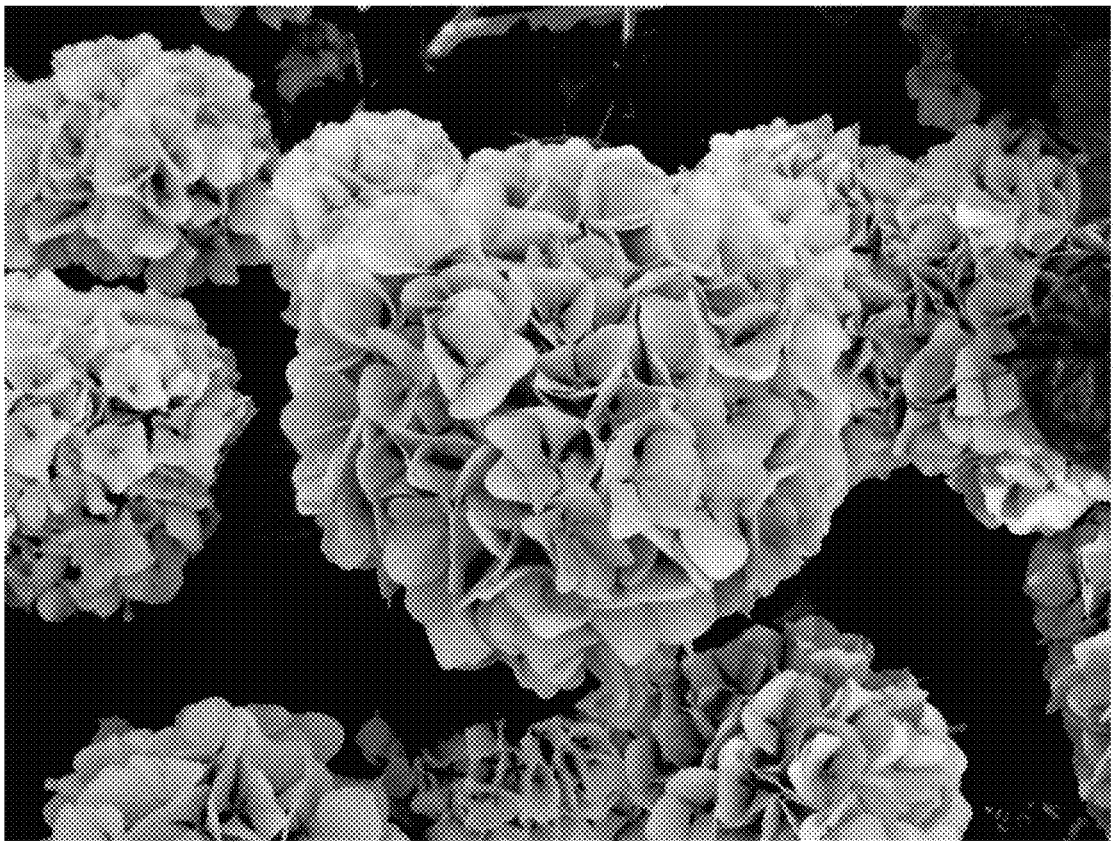
Figure 2:
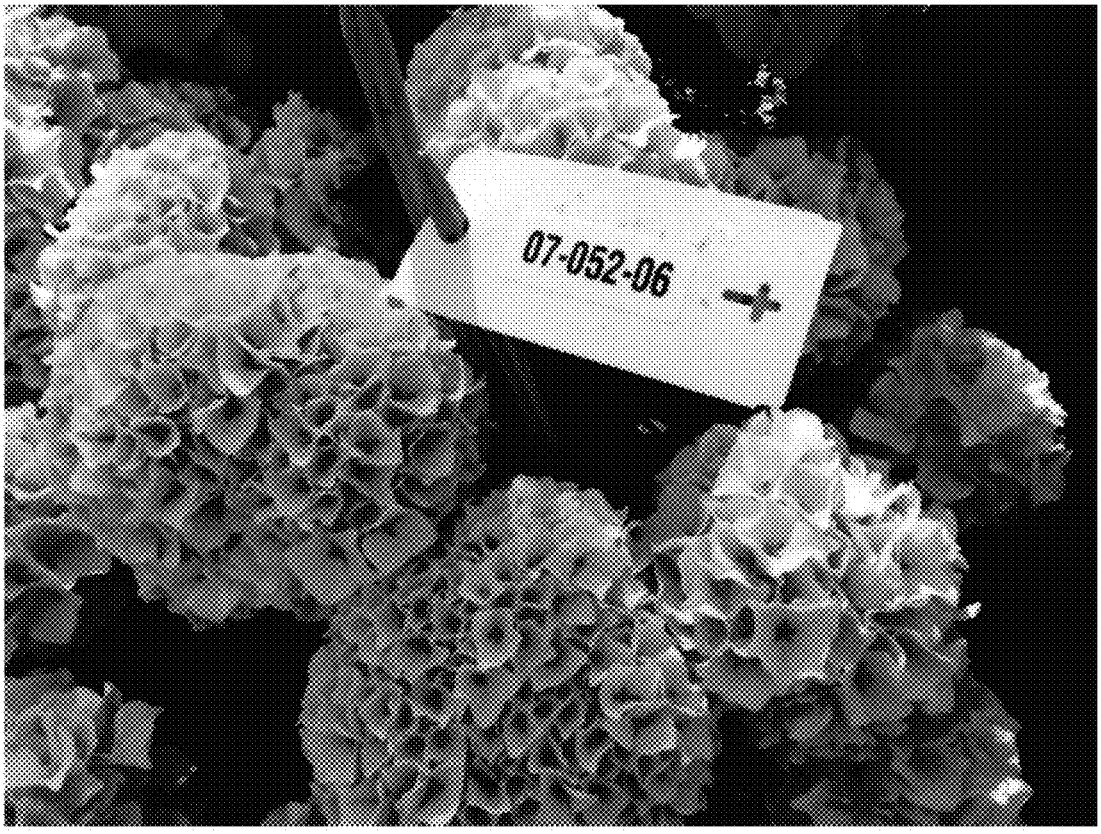

The photograph in FIG. 2 provides a view of the inflorescences of 'Hokomapfloy' when grown under non-bluing conditions.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of 2-year-old plants of 'Hokomapfloy' as grown outdoors in 2-gallon containers in Dayton, Oregon and grown under bluing conditions (with exception of sterile sepal color provided as well when grown under non-bluing conditions). The color determination is in accordance with The 2015 Colour Chart of The Royal Horticultural Society, London, England, except where general color terms of ordinary dictionary significance are used.

General description:

*Blooming period*.—June and July in The Netherlands with flowers showy at least for 2 months.

*Plant type*.—Deciduous shrub, mophead type *Hydrangea*.

*Plant habit*.—Compact, densely branched, rounded.

*Height and spread*.—54 cm in in height and 85 cm in width as an 18-month old plant grown in a 2-gallon container, reached 1 m in height and spread as a 3-year-old plant in the landscape.

*Hardiness*.—At least in U.S.D.A. Zones 5 to 9.

*Diseases and pests*.—No susceptibility and resistance to diseases or pests has been observed.

*Root description*.—Fine and fibrous, 161C in color.

*Propagation*.—Stem cuttings.

*Root development*.—An average of 6 weeks for root initiation with a young rooted plant produced in an average of 18 weeks.

*Growth rate and vigor*.—Moderate.

Branch description:

*Branch shape*.—Round to flattened oval.

*Branch strength*.—Main; strong, lateral; moderately strong and bendable.

*Branch color*.—Young and mature; 146C in color, random linear flushes of 187A, base of branches moderately covered with linear lenticels 1 mm in length, 200A in color, older woody branches and bark; 196A and 199A.

*Branch size*.—Main branches; an average of 9 cm in length, 2 cm in diameter, lateral branches; average of 29 cm in length and 5 mm in diameter.

*Branch surface*.—Young and mature; glossy, glabrous, older woody branches and old bark; exfoliating, matte, dry.

*Branch aspect*.—Upright to outward, winding.

*Internode length*.—An average of 7 cm.

*Branching*.—Densely branched; 6 main branches, up to 15 lateral branches per main branch.

Foliage description:

*Leaf shape*.—Ovate.

*Leaf arrangement*.—Opposite.

*Leaf division*.—Simple.

*Leaf base*.—Acute.

*Leaf apex*.—Abruptly acuminate.

*Leaf margins*.—Serrate.

*Leaf venation*.—Pinnate, color; upper surface non-distinguishable, main vein 157A, lower surface; 144B.

*Leaf size*.—An average of 11 cm in length and 7 cm in width.

*Leaf attachment*.—Petiolate.

*Leaf number*.—An average of 10 per lateral stem.

*Leaf surface*.—Both surfaces glabrous, matte with a slight sheen.

*Leaf color*.—Young foliage upper and lower surface 144A to 144B, mature foliage upper surface 137A and NN137A, mature foliage lower surface 147B.

*Petioles*.—An average of 2 cm in length and 5 mm in diameter, both surfaces are smooth and slightly glossy and 146C in color.

Inflorescence description:

*Inflorescence type*.—Terminal panicle, flattened mophead comprised of a sterile flowers above fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 8 cm in height and 11 cm in diameter.

*Flower number*.—Per mophead; an average of 80 sterile flowers and 16 fertile flowers.

*Flower fragrance*.—None.

*Flower aspect*.—Upright to slightly nodding.

*Flower size*.—Sterile flowers; an average of 3.5 cm in diameter and 1.5 cm in depth, fertile flowers; an average of 8 mm in diameter and 5 mm in depth.

*Flower type*.—Rotate.

*Flower buds*.—Sterile and fertile flowers; an average of 3 mm in length, 2 mm in diameter, rounded to oval in shape, 145A and 144A in color.

*Peduncles*.—Moderately strong, bendable, flattened oval in shape, an average of 1 cm in length and 3 mm in width, glossy, glabrous, color: young; 146C in color with random linear flushes of 187A, mature; 143A, occasionally flushed with N77A.

*Pedicels*.—Sterile flowers; moderately strong, bendable, rounded in shape, an average of 1.5 cm in length and 2 mm in diameter, matte and satiny surface, color; 145B to 145D, fertile flowers; moderately strong, bendable, rounded in shape, an average of 5 mm in length and 0.8 mm in diameter, matte and satiny surface, color: young; 145A, mature; a blend of 65A, 68A, and N88A.

*Petals*.—Sterile flowers: petal spot; 1 mm in depth and diameter, flattened and round in shape, color: when young 157A, mature (under non-bluing conditions) 65A, (under non-bluing conditions) 97A to 97C, fertile flowers: petal spot; round 4 mm in diameter and depth, rounded in shape, 157A, when fully open inner and outer surface; 97C and 97A in color.

*Sepals*.—Sterile flowers; 4, rotate and overlapping, apex slightly emarginate to obtuse, base is squared, margins are slightly undulate, deltoid and cup-shaped, an average of 2 cm in length and 1.7 cm in width (at the widest point), both surface glabrous, velvety and matte, moderate thickness, color: when opening upper and lower surface; at burst 142A to 142B, as the sepals open (under non-bluing conditions) 150C to 150D to NN155A and NN155D, tips lightly flushed with 65B, (under bluing conditions) 150C to 150D to NN155A and NN155D, when sepals are fully open upper and lower surface; (under non-bluing conditions) 65C, base 65A, (under bluing conditions) 92C to 92D, slight hues of 92A, base lightly flushed with N80B, fertile flowers; 4, fused base, apex is acute, an average of 1 mm in length and 1 mm in width (at the widest point), both surfaces glabrous, 4B in color.

Reproductive organs:

*Gynoecium*.—Sterile flowers; 1 pistil, stigma; club-shaped, bifid, N82B in color, 0.5 mm in length, 1 mm in width, style; 0.75 mm in length, N82B in color, ovary is superior, 3 mm in depth, 1 mm in diameter, N155A in color, fertile flowers; 3 pistils, an average of 2 mm in length, stigma; club-shaped and 108A in color, style; 0.75 mm in length, 108A in color, ovary is superior, 3 mm in depth, 1 mm in diameter, N155A in color.

*Androecium*.—Sterile flowers; an average of 6 stamens, filaments; an average of 2 mm in length and 96B in color, anthers; oblong and flattened in shape, an average of 1.5 mm in width, 1 mm in depth, 4A in color, pollen; low in quantity, 8C in color, fertile flowers; an average of 10 stamens, filaments; an average of 2 mm in length and 105A in color, anthers; broad oblong in shape, an average of 0.7 mm in width, 0.5 in depth, NN155A in color, pollen; none observed.

*Fruit and seed*.—None observed to date.

It is claimed:

1. A new and distinct cultivar of *Hydrangea* plant named 'Hokomapfloy' substantially as herein illustrated and described.

* * * * *